United States Patent
Butterick, III et al.

(10) Patent No.: US 9,422,493 B2
(45) Date of Patent: Aug. 23, 2016

(54) TRITYLATED ALKYL ARYL ETHERS

(71) Applicants: Rohm and Haas Company, Philadelphia, PA (US); Dow Global Technologies LLC, Midland, MI (US)

(72) Inventors: Robert Butterick, III, Swedesboro, NJ (US); George David Green, Cary, IL (US); Raymond J. Swedo, Mount Prospect, IL (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/590,130

(22) PCT Filed: Jul. 1, 2013

(86) PCT No.: PCT/US2013/048881
§ 371 (c)(1),
(2) Date: Jan. 6, 2015

(87) PCT Pub. No.: WO2014/008164
PCT Pub. Date: Jan. 9, 2014

(65) Prior Publication Data
US 2016/0194571 A1    Jul. 7, 2016

Related U.S. Application Data

(60) Provisional application No. 61/668,535, filed on Jul. 6, 2012.

(51) Int. Cl.
| | |
|---|---|
| *C10L 1/18* | (2006.01) |
| *C10L 1/00* | (2006.01) |
| *C10L 1/185* | (2006.01) |
| *C10L 1/183* | (2006.01) |
| *C07C 43/205* | (2006.01) |
| *C07C 39/15* | (2006.01) |

(52) U.S. Cl.
CPC ............ C10L 1/003 (2013.01); C07C 39/15 (2013.01); C07C 43/205 (2013.01); C10L 1/1832 (2013.01); C10L 1/1852 (2013.01)

(58) Field of Classification Search
CPC ..... C10L 1/003; C10L 1/1852; C10L 1/1832; C07C 43/205; C07C 39/15
See application file for complete search history.

(56) References Cited

U.S. PATENT DOCUMENTS

| | | | |
|---|---|---|---|
| 5,981,283 | A | 11/1999 | Anderson, II et al. |
| 7,858,373 | B2 | 12/2010 | Banavali et al. |
| 9,012,706 | B2 * | 4/2015 | Green ............... C07C 43/20 44/440 |
| 2010/0196242 | A1 | 8/2010 | Stanic et al. |
| 2014/0123549 | A1 | 5/2014 | Green et al. |

FOREIGN PATENT DOCUMENTS

| | | |
|---|---|---|
| EP | 489492 A1 | 6/1992 |
| EP | 512404 | 11/1992 |
| WO | 2012154646 A1 | 11/2012 |
| WO | 2012154668 A1 | 11/2012 |
| WO | WO2012177987 * | 12/2012 |
| WO | 2013/116582 A1 | 8/2013 |

OTHER PUBLICATIONS

"Index of subjects", J. Chemical Society (Resumed), p. 3012 (1929).
Barroeta, et al., "Kinetics and Substituent Effects in Electrophilic Aromatic Substitution. II. Tritylation of Catechol and its Monoether", vol. 31, pp. 2330-2333, (1966).
Chuchani, "Chuchani: Tritylation of ortho-Disubstituted Benzenes", J. Chem. Soc., pp. 1753-1756 (1959).
Chuchani, "Condensation of Chlorotriphenylmethane with ortho-Disubstituted Benzenes. Further Evidence on the Systematic Difference of Activation of ortho- and para-Directing Groups." J. Chem. Soc., pp. 325-326 (1960).
Chuchani, et al., "Kinetics and Substituent Effects in Electrophillic", J. Organic Chemistry, vol. 31, No. 5, pp. 1573-1576 (1966).
Clapp, "The Aldehydic Constituents from the Ethanolysis of Spruce and Maple Woods", J. American Chemical Society, vol. 61, No. 2, pp. 523-524 (1939).
Cook, et al., "Oxidation of Hindered Phenols. X. Effect of 4-Substituents upon the Behavior of 2,6-Di-t-butylphenoxy Radicals", Notes, pp. 1429-1431 (1960).
Iddles, et al., "Rearrangement of the Triphenylmethyl Ether of Ortho Cresol: Direct Synthesis of 3-Methyl-4-methoxyphenyltriphenylmethane", Dept. of Chemistry, University of New Hampshire, pp. 2757-2759 (1940).
Llewellyn, et al., "The Condensation of Some Tertiary Aryl Substituted Carbinols with Phenol in the Presence of Aluminum Chloride", vol. 60, pp. 59-62, (1938).
Nandanwar, et al., "Formation of Ruthenium Nanoparticles by the Mixing of Two Reactive Microemulsions," IEC, vol. 50, pp. 1145-1151 (2011).
Schoepfle, et al., "The Reaction between Triarylmethyl Halides and Phenylmagnesium Bromide. II", vol. 58, pp. 791-794 (1936).
Varin, et al., "Structural stability of sodium borohydride (NaBH4) during controlled mechanical milling," J. Alloys and Compounds, vol. 397 pp. 276-281 (2005).
Shulgin, "The Baeyer-Villiger Condensation. I. ortho-Tritylation of Phenols", TDCC, Western Division, Pittsburg, CA, vol. 27, pp. 3868-3872 (1962).

* cited by examiner

*Primary Examiner* — Cephia D Toomer
(74) *Attorney, Agent, or Firm* — Kenneth Crimaldi

(57) ABSTRACT

A compound having formula $(Ph_3C)_mAr(R^1)_j(OR^2)_n$, wherein Ph represents a phenyl group, Ar is an aromatic ring system having from six to twenty carbon atoms, $R^1$ and $R^2$ independently are $C_1$-$C_{18}$ alkyl or $C_4$-$C_{18}$ heteroalkyl, m is one or two, j is an integer from one to four and n is an integer from one to three.

7 Claims, No Drawings

TRITYLATED ALKYL ARYL ETHERS

This invention relates to new compounds useful in a method for marking liquid hydrocarbons and other fuels and oils.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a compound having formula $(Ph_3C)_m Ar(R^1)_j(OR^2)_n$, wherein Ph represents a phenyl group, Ar is an aromatic ring system having from six to twenty carbon atoms, $R^1$ and $R^2$ independently are $C_1$-$C_{18}$ alkyl or $C_4$-$C_{18}$ heteroalkyl, m is one or two, j is an integer from one to four and n is an integer from one to three.

The present invention further provides a method for marking a petroleum hydrocarbon or a liquid biologically derived fuel; said method comprising adding to said petroleum hydrocarbon or liquid biologically derived fuel at least one compound having formula $(Ph_3C)_m Ar(R^1)_j(OR^2)_n$, wherein Ph represents a phenyl group, Ar is an aromatic ring system having from six to twenty carbon atoms, $R^1$ and $R^2$ independently are $C_1$-$C_{18}$ alkyl or $C_4$-$C_{18}$ heteroalkyl, m is one or two, j is an integer from one to four and n is an integer from one to three; wherein each compound having formula $(Ph_3C)_m Ar(R^1)_j(OR^2)_n$ is present at a level from 0.01 ppm to 20 ppm.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol."

An "alkyl" group is a substituted or unsubstituted hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are saturated. Preferably, alkyl groups are unsubstituted. Preferably, alkyl groups are linear or branched. An "aryl" group is a substituent derived from an aromatic hydrocarbon compound. An aryl group has a total of from six to twenty ring atoms, unless otherwise specified, and has one or more rings which are separate or fused. Substitution on aryl groups of one or more alkyl or alkoxy groups is permitted. A "heteroalkyl" group is an alkyl group in which one or more methylene groups has been replaced by O or S. Preferably, heteroalkyl groups contain from one to six O or S atoms, preferably from one to four, preferably from one to three. The methylene groups replaced by O or S were bonded to two other carbon atoms in the corresponding alkyl group. Preferably, heteroalkyl groups do not contain S atoms. Preferably, heteroalkyl groups are saturated. Heteroalkyl groups may be substituted by OH or $C_1$-$C_{18}$ alkoxy groups, preferably OH or $C_1$-$C_6$ alkoxy groups, preferably hydroxy or $C_1$-$C_4$ alkoxy groups. Examples of heteroalkyl groups include oligomers of ethylene oxide, propylene oxide or butylene oxide having two to six units of the alkylene oxide (preferably two to four, preferably two or three) and a terminal hydroxy or $C_1$-$C_6$ alkoxy group (preferably hydroxy or $C_1$-$C_4$ alkoxy, preferably hydroxy or methoxy, preferably hydroxy); an example of an ethylene oxide oligomer is $-\{(CH_2)_2O\}_x R^3$, where x is an integer from two to six and $R^3$ is hydrogen or $C_1$-$C_6$ alkyl. Preferably, j is from two to four, preferably two or three. Preferably, $R^3$ is hydrogen or $C_1$-$C_4$ alkyl, preferably hydrogen or methyl, preferably hydrogen. Preferably, the compounds of this invention contain elements in their naturally occurring isotopic proportions.

Ar is an aromatic ring system having from six to twenty carbon atoms and whose substituents include $Ph_3C$, $R^1$ and $OR^2$ groups, preferably one in which the only substituents are $Ph_3C$, $R^1$ and $OR^2$ groups. Preferably, Ar is a $C_6$-$C_{12}$ hydrocarbyl aromatic ring system. Preferably, Ar is benzene, naphthalene, biphenyl, phenyl ether, diphenylmethane or one of the preceding systems substituted with alkyl and/or alkoxy groups; preferably benzene. Preferably, n is one or two, preferably one. Preferably, m is one. Preferably, j is from one to three, preferably one or two. Preferably, $R^1$ is $C_2$-$C_{12}$ alkyl or $C_4$-$C_{12}$ heteroalkyl, preferably $C_2$-$C_{12}$ alkyl, preferably $C_3$-$C_8$ alkyl or $C_4$-$C_8$ heteroalkyl, preferably $C_2$-$C_8$ alkyl, preferably $C_3$-$C_8$ alkyl, preferably $C_3$-$C_6$ alkyl, preferably $C_2$-$C_6$ alkyl, preferably $C_2$-$C_5$ alkyl, preferably sec-butyl, t-butyl or isopropyl. Preferably, $R^1$ is saturated. Preferably, $R^1$ is linear or branched. Preferably, $R^2$ is $C_2$-$C_{18}$ alkyl or $C_4$-$C_{18}$ heteroalkyl, preferably $C_4$-$C_{18}$ alkyl or $C_4$-$C_{18}$ heteroalkyl, preferably $C_2$-$C_{18}$ alkyl, preferably $C_3$-$C_{18}$ alkyl or $C_4$-$C_{12}$ heteroalkyl, preferably $C_3$-$C_{18}$ alkyl, preferably $C_4$-$C_{18}$ alkyl, preferably $C_6$-$C_{18}$ alkyl, preferably $C_6$-$C_{16}$ alkyl, preferably $C_{10}$-$C_{14}$ alkyl. Preferably, $R^2$ is saturated. Preferably, $R^2$ is linear or branched, preferably branched.

In using the compounds of this invention as markers, preferably the minimum amount of each compound added to a liquid to be marked is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectable by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art, e.g., alkylation of alkyl phenols or alkyl polyhydroxyaromatics with trityl halide or alcohol, followed by alkylation with organic halides in the presence of base. For example, tritylated alkyl phenolic ethers may be prepared according to the following reaction scheme,

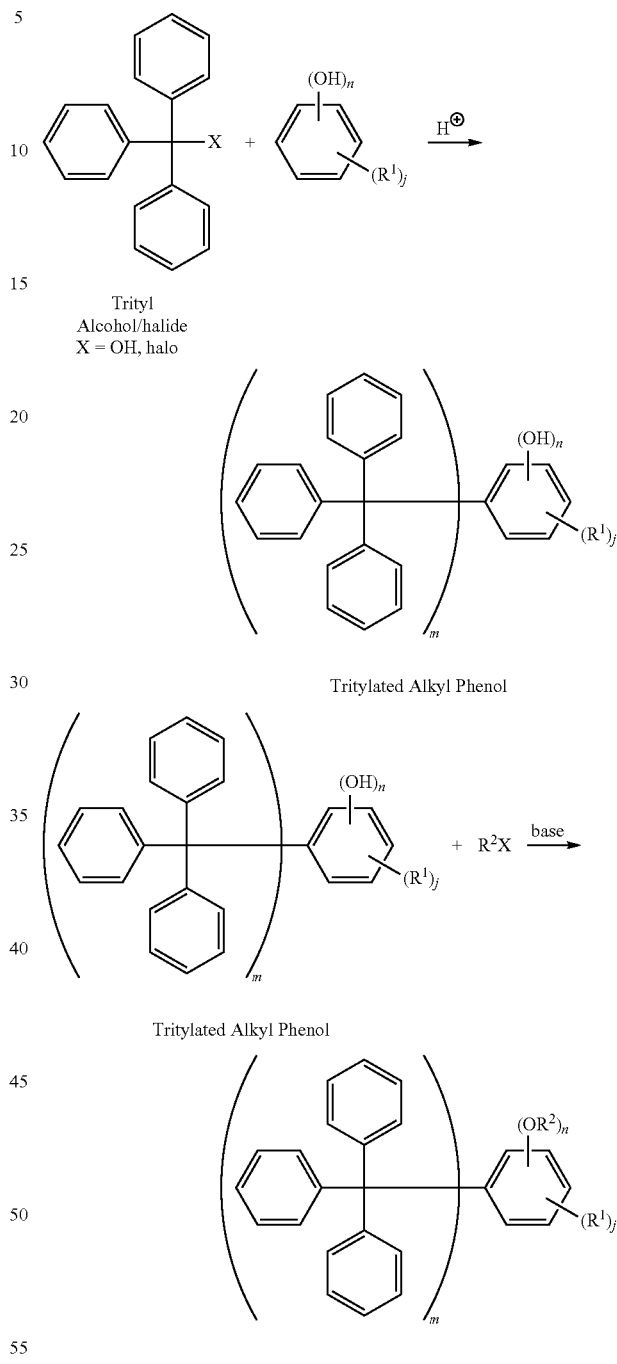

Trityl
Alcohol/halide
X = OH, halo

Tritylated Alkyl Phenol

Tritylated Alkyl Phenol

Tritylated Alkyl Phenol Ether

Corresponding compounds in which Ar is not benzene may be prepared from the corresponding substituted aromatic starting materials.

Examples

A typical procedure for the synthesis of a trityl alkyl phenol is illustrated by:

2-(sec-Butyl)-4-tritylphenol

A 250 mL 1-neck flask was equipped with a magnetic stirrer and a reflux condenser with nitrogen blanket. The flask was charged with 6.52 grams (0.025 moles) of trityl alcohol, 3.77 grams (0.025 moles) of o-sec-butylphenol, and 50 mL of glacial acetic acid. The mixture was stirred under nitrogen at room temperature to give a clear, yellow solution. Concentrated sulfuric acid (5 mL) was then added in one portion. The solution immediately became dark red-brown. The solution was stirred at room temperature for 2 days, during which time solids separated out. The reaction mixture was filtered, and the solids were washed on the filter with several portions of water. After drying in a vacuum oven at 65° C. for 3 hours, the yield of product was 7.34 grams (75% yield). MP=135-136° C. GPC analysis showed a purity of >99%. The structure was confirmed by IR, $^1$H- and $^{13}$C-NMR analyses.

The trityl alkyl phenol compounds prepared by this procedure are listed in Table 1 below.

TABLE 1

Synthesis Data for Trityl Alkyl Phenols

| Trityl Phenol (T = triphenylmethyl) | Mol. Wt. | MP, ° C. | % Yield | [CAS] |
|---|---|---|---|---|
| [structure] | 392.53 | 136-136 | 75 | (none) |
| [structure] | 448.64 | 82-91 | 94 | (none) |
| [structure] | 392.52 | 181-182 | 93 | 60043-12-1 |
| [structure] | 392.52 | 153-161 | 35 | 97358-11-7 |
| [structure] | 448.64 | 157-161 | 89 | 68869-56-7 |
| [structure] | 448.64 | 188-200 | 16 | (none) |
| [structure] | 378.51 | 145-147 | 82 | (none) |
| [structure] | 420.59 | 142-143 | 91 | (none) |

A typical procedure for the synthesis of a trityl alkyl aryl ether is illustrated by:

(3-(sec-Butyl)-4-(decyloxy)phenyl)methanetrityl) tribenzene (DecTsBuPh

A 500 mL 3-neck flask was equipped with a magnetic stirrer, a reflux condenser with nitrogen blanket, a heating mantle with a temperature controller, and a thermocouple. The flask was charged with 39.32 grams (0.1 mole) of TritosBuPhOH, 6.64 grams (0.1 mole) of 85% potassium hydroxide pellets, and with 250 mL of dimethyl sulfoxide. The mixture was stirred under nitrogen while being heated to 110° C. When all of the potassium hydroxide had dissolved, the dark colored reaction mixture was cooled to 50° C. Bromodecane (20.7 mL, 22.12 grams, 0.1 mole) was then added in one portion. An exotherm to about 60° C. was observed. Heating at 60° C. was maintained for 8 hours, then the reaction mixture was poured into about 1200 mL of water containing about 2 grams of potassium hydroxide pellets and about 15 grams of sodium chloride. Toluene (about 300 mL) was added, and the mixture was stirred at room temperature for about 1 hour. The mixture was transferred to a separatory funnel, and the layers were separated. The aqueous layer was washed with 1×100 mL of toluene, and the washings were combined with the original toluene layer. The toluene solution was dried over anhydrous magnesium sulfate. After filtration, the toluene was removed by rotary evaporation to give 49.48 grams of product as a red oil. Yield was 93%. The structure was confirmed by IR, $^1$H-$^{13}$C-NMR, and GC/MS analyses.

GC/MS Studies:

Stock solutions of each candidate were prepared in dichloromethane (DCM). These solutions were used to establish GC retention times and MS fragmentation patterns, to determine linearity vs. concentration curves from 100 to 1000 ppb, and to demonstrate repeatability and accuracy at 500 ppb concentrations. GC/MS results are shown in Tables 2 and 3.

GC/MS Parameters:

Column: Agilent DB 35 m, 15.0 m×0.25 mm×0.25μ

Flow Rate: 1.5 mL/min. He carrier gas

Oven: initial: 100° C.

Ramp 1: 20° C./min. to 280° C.; Hold: 10 min.

Ramp 2: 20° C./min. to 340° C.; Hold: 6 min.

Inlet Temp.: 280° C.

Insert: Splitless; Vent: 15 min., Single taper, glass wool, deactivated, 5062-3587

Injection Volume: 3 μL; Viscosity: 5 sec., Plunger: fast

Mass Transfer Line Temp.: 280° C.

MS Quad: 200° C.; MS Source: 250° C.

Solvent Delay: 18.5 min.

TABLE 2

Synthesis Data for Trityl Alkyl o-sec-Butyl Phenol Ethers

| $R_2$ | Mol. Wt. | MP, °C. | % Yield | GC Ret Time min. | MS Major Mass, m/e |
|---|---|---|---|---|---|
| n-$C_6H_{13}$ | 476.69 | 93-97 | 81 | 14.2 | 476, 399 |
| n-$C_{10}H_{21}$ | 532.81 | oil | 93 | 20.99 | 532, 455 |
| n-$C_{12}H_{25}$ | 560.85 | oil | 87 | 22.25 | 560, 483 |
| n-$C_{14}H_{29}$ | 588.9 | oil | 88 | 23.49 | 588, 511 |
| n-$C_{16}H_{33}$ | 616.96 | 49-54 | 82 | 25.16 | 616, 539 |

TABLE 3

Synthesis Data for Trityl Dodecyl Aryl Ethers

| Trity Dodecyl Aryl Ether (T = triphenylmethyl) | Mol. Wt. | MP, °C. | % Yield | GC Ret Time min. | MS Major Mass, m/e |
|---|---|---|---|---|---|
| 2,6-di-sec-butyl-4-trityl phenyl dodecyl ether | 616.96 | oil | 79 | 20.91 | 616, 539, 371 |
| 2-tert-butyl-4-trityl phenyl dodecyl ether | 560.85 | oil | 100 | 22.32 | 560, 483, 315 |
| 4-tert-butyl-2-trityl phenyl dodecyl ether | 560.85 | oil | 100 | 19.96 | 560, 377 |
| 2,6-di-tert-butyl-4-trityl phenyl dodecyl ether | 616.96 | oil | 75 | 21.41 | 616, 371 |
| 2,4-di-tert-butyl-6-trityl phenyl dodecyl ether | 616.96 | 114-119 | 43 | 616 | 448, 433 |

TABLE 3-continued

Synthesis Data for Trityl Dodecyl Aryl Ethers

| Trity Dodecyl Aryl Ether (T = triphenylmethyl) | Mol. Wt. | MP, ° C. | % Yield | GC Ret Time min. | MS Major Mass, m/e |
|---|---|---|---|---|---|
| 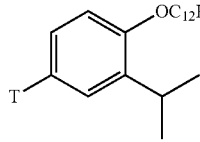 | 546.84 | 49-51 | 91 | 22.03 | 546, 469, 301 |
| 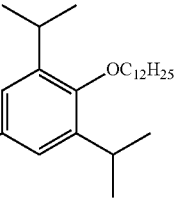 | 588.9 | oil | 91 | 20.64 | 588, 511, 343 |

TABLE 4

Stability and Extractability* Data for DecTsBuPh

| | % Change |
|---|---|
| Standard | 0.00 |
| 5% NaOH | 0.10 |
| 50% NaOH | 0.60 |
| 5% $H_2SO_4$ | −0.04 |
| 98% $H_2SO_4$ | −1.84 |
| 2% Charcoal | −0.76 |
| 5% Bleach | 1.08 |
| Iron Specks | 1.76 |
| Fuller's Earth | 0.79 |

*Test Protocols: 2000 mg/kg solution with internal standard was made in xylenes, then dosed with 5% by weight of 5% NaOH, 50% NaOH, 5% sulfuric acid and 98% sulfuric acid. It was also tested with 2% charcoal 5% bleach and 2% metal specs by wt/wt. The mixtures were stirred gently at room temperature for 8 hours, then the solutions were analyzed by GC and compared to the stock solution.

TABLE 5

Sunlight Stability Data* for DecTsBuPh

| Sunlight | % Change |
|---|---|
| Standard | 0.00 |
| Apr. 5, 2012 | −1.90 |
| Apr. 13, 2012 | 2.40 |
| Apr. 23, 2012 | 0.90 |
| May 8, 2012 | −1.40 |
| May 15, 2012 | 1.80 |

*The marker sample was made at 2000 mg/.1 concentration with internal standard and checked by GC every week for changes in marker concentration.

Solubility Studies:

Solutions were made from 0.1 grams of marker candidate and 0.9 grams of solvent. The mixtures were warmed briefly to 60° C. to completely dissolve the marker candidate, then the solutions were cooled to room temperature. The solutions were then placed into a −10° C. freezer, and the stability of the solutions was monitored for at least 7 days.

TABLE 6

Solubility Data for Trityl Alkyl o-sec-Butyl Phenol Ethers

| $R_2$ | SOLVENT | SOLUBILITY BEHAVIOR[a] 60 C. | ROOM TEMP | −10 C. |
|---|---|---|---|---|
| $C_6H_{13}$ | Aromatic 200 | sol | sol | xtls 4D |
| | DPGDME | sol | sol | xtls 4D |
| | tetralin | sol | sol | xtls 5D |
| | NMP | sol | sol | xtls 5D |
| | DMAc | sol | sol | xtls 4D |
| | 75:25 Aromatic 150: cyclohexanone | sol | sol | sol 7D |
| $C_{10}H_{23}$ | Aromatic 200 | sol | sol | sol 33D |
| | DPGDME | sol | sol | sol 33D |
| | tetralin | sol | sol | sol 33D |
| | NMP | sol | sol | sol 33D |
| | DMAc | sol | sol | sol 33D |
| | 75:25 Aromatic 200: cyclohexanone | sol | sol | sol 33D |
| | 75:25 Aromatic 150: cyclohexanone | sol | sol | sol 33D |
| $C_{12}H_{25}$ | Aromatic 200 | sol | sol | xtls 6D |
| | DPGDME | sol | sol | sol 7D |
| | tetralin | sol | sol | sol 7D |
| | NMP | sol | sol | sol 7D |
| | DMAc | sol | sol | sol 7D |
| | 75:25 Aromatic 150: cyclohexanonesol | sol | sol | sol 7D |
| $C_{14}H_{29}$ | Aromatic 200 | sol | sol | sol 7D |
| | DPGDME | sol | sol | sol 7D |
| | tetralin | sol | sol | sol 7D |
| | NMP | sol | sol | sol 7D |
| | DMAc | sol | sol | xtls 6D |
| | 75:25 Aromatic 150: cyclohexanone | sol | sol | sol 7D |

TABLE 6-continued

Solubility Data for Trityl Alkyl o-sec-Butyl Phenol Ethers

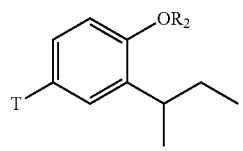

| R$_2$ | SOLVENT | 60 C. | ROOM TEMP | −10 C. |
|---|---|---|---|---|
| C$_{16}$H$_{33}$ | Aromatic 200 | sol | sol | sol 7D |
| | DPGDME | sol | sol | sol 7D |
| | tetralin | sol | sol | sol 7D |
| | NMP | sol | sol | xtls 6D |
| | DMAc | sol | sol | xtls 6D |
| | 75:25 Aromatic 150: cyclohexanone | sol | sol | sol 7D |

$^a$sol = soluble; xtls = crystals; D = days

DPGME is dipropylene glycol mono-methyl ether and NMP is N-methylpyrrolidone; AROMATIC 200 and AROMATIC 150 are mixed aromatic solvents available from Exxon Mobil Corp.

TABLE 7

Solubility Data for Trityl Dodecyl Aryl Ethers

| Trity Dodecyl Aryl Ether (T = triphenylmethyl) | SOLVENT | 60 C. | ROOM TEMP | −10 C. |
|---|---|---|---|---|
| [2,6-di-sec-butyl-4-T phenyl dodecyl ether] | 75:25 Aromatic 200H: cyclohexanone | sol | sol | sol 7D |
| | 75:25 Aromatic 200H: o-sec-butylphenol | sol | sol | sol 7D |
| [2-tert-butyl-4-T phenyl dodecyl ether] | 75:25 Aromatic 200H: cyclohexanone | sol | sol | sol 7D |
| | 75:25 Aromatic 200H: o-sec-butylphenol | sol | sol | sol 7D |
| [3-T phenyl dodecyl ether with tert-butyl] | 75:25 Aromatic 200H: cyclohexanone | sol | sol | sol 7D |
| | 75:25 Aromatic 200H: o-sec-butylphenol | sol | sol | sol 7D |
| [2,6-di-tert-butyl-4-T phenyl dodecyl ether] | 75:25 Aromatic 200H: cyclohexanone | sol | sol | sol 7D |
| | 75:25 Aromatic 200H: o-sec-butylphenol | sol | sol | sol 7D |

TABLE 7-continued

Solubility Data for Trityl Dodecyl Aryl Ethers

| Trityl Dodecyl Aryl Ether (T = triphenylmethyl) | SOLVENT | SOLUBILITY BEHAVIOR$^a$ 60 C. | ROOM TEMP | −10 C. |
|---|---|---|---|---|
| [structure: 2,6-di-tert-butyl-4-trityl phenyl dodecyl ether] | 75:25 Aromatic 200H: cyclohexanone | sol | sol | xtls 6D |
| | 75:25 Aromatic 200H: o-sec-butylphenol | sol | sol | xtls 6D |
| [structure: 2-isopropyl-4-trityl phenyl dodecyl ether] | 75:25 Aromatic 200H: cyclohexanone | sol | sol | sol 7D |
| | 75:25 Aromatic 200H: o-sec-butylphenol | sol | sol | xtls 3D |
| [structure: 2,6-diisopropyl-4-trityl phenyl dodecyl ether] | 75:25 Aromatic 200H: cyclohexanone | sol | sol | xtls 4D |
| | 75:25 Aromatic 200H: o-sec-butylphenol | sol | sol | sol |

$^a$sol = soluble;
xtls = crystals
D = days

The invention claimed is:

1. A compound having formula $(Ph_3C)_m Ar(R^1)_j(OR^2)_n$, wherein Ph represents a phenyl group, Ar is a $C_6$-$C_{12}$ hydrocarbyl aromatic ring system, $R^1$ is $C_2$-$C_{12}$ alkyl or $C_4$-$C_{12}$ heteroalkyl, $R^2$ is $C_4$-$C_{18}$ alkyl or $C_4$-$C_{18}$ heteroalkyl, m is one or two, j is an integer from one to three and n is an integer from one to two.

2. The compound of claim 1 in which Ar is a benzene ring system, j is one or two, n is one, $R^1$ is $C_2$-$C_8$ alkyl, $R^2$ is $C_4$-$C_{18}$ alkyl and m is one.

3. A method for marking a petroleum hydrocarbon or a liquid biologically derived fuel; said method comprising adding to said petroleum hydrocarbon or liquid biologically derived fuel at least one compound having formula $(Ph_3C)_m Ar(R^1)_j(OR^2)_n$, wherein Ph represents a phenyl group, Ar is an aromatic ring system having from six to twenty carbon atoms, $R^1$ and $R^2$ independently are $C_1$-$C_{18}$ alkyl or $C_4$-$C_{18}$ heteroalkyl, m is one or two, j is an integer from one to four and n is an integer from one to three; wherein each compound having formula $(Ph_3C)_m Ar(R^1)_j(OR^2)_n$ is present at a level from 0.01 ppm to 20 ppm.

4. The method of claim 3 in which Ar is a $C_6$-$C_{12}$ hydrocarbyl aromatic ring system, j is an integer from one to three and n is one or two.

5. The method of claim 4 in which $R^1$ is $C_2$-$C_{12}$ alkyl or $C_4$-$C_{12}$ heteroalkyl.

6. The method of claim 5 in which $R^2$ is $C_4$-$C_{18}$ alkyl or $C_4$-$C_{18}$ heteroalkyl.

7. The method of claim 6 in which Ar is a benzene ring system, j is one or two, n is one, $R^1$ is $C_2$-$C_8$ alkyl, $R^2$ is $C_4$-$C_{18}$ alkyl and m is one.

* * * * *